(12) United States Patent
Ding et al.

(10) Patent No.: US 11,293,879 B2
(45) Date of Patent: Apr. 5, 2022

(54) DRY SLIDE ASSAY USING REDUCED READING WINDOW

(71) Applicant: Ortho-Clinical Diagnostics, Inc., Raritan, NJ (US)

(72) Inventors: Zhong Ding, Pittsford, NY (US); Andrew M. Kirsch, Webster, NY (US); Edward R. Scalice, Penfield, NY (US); Benjamin Wojtasiewicz, Raritan, NJ (US)

(73) Assignee: ORTHO-CLINICAL DIAGNOSTICS, INC., Raritan, NJ (US)

( * ) Notice: Subject to any disclaimer, the term of this patent is extended or adjusted under 35 U.S.C. 154(b) by 462 days.

(21) Appl. No.: 16/458,474

(22) Filed: Jul. 1, 2019

(65) Prior Publication Data

US 2020/0003699 A1  Jan. 2, 2020

Related U.S. Application Data

(60) Provisional application No. 62/693,120, filed on Jul. 2, 2018.

(51) Int. Cl.
| | |
|---|---|
| *G01N 21/93* | (2006.01) |
| *G01N 21/01* | (2006.01) |
| *G01N 21/03* | (2006.01) |
| *G01N 33/52* | (2006.01) |

(52) U.S. Cl.
CPC ............ *G01N 21/93* (2013.01); *G01N 21/01* (2013.01); *G01N 33/525* (2013.01); *G01N 2021/0106* (2013.01); *G01N 2021/0389* (2013.01)

(58) Field of Classification Search
CPC ... G01N 2021/0106; G01N 2021/0389; G01N 2021/178; G01N 21/01; G01N 21/77; G01N 21/8483; G01N 21/93; G01N 33/48; G01N 33/525; Y10T 436/25; Y10T 436/25125; Y10T 436/2575
USPC ....... 436/164, 165, 169, 170, 174, 175, 180; 422/400–403, 420–424, 82.05, 82.09, 563
See application file for complete search history.

(56) References Cited

U.S. PATENT DOCUMENTS

| | | | | |
|---|---|---|---|---|
| 5,508,200 | A * | 4/1996 | Tiffany | ................. B82Y 30/00 436/44 |
| 2008/0259321 | A1* | 10/2008 | Lea | ..................... G01N 33/582 356/213 |
| 2008/0316466 | A1* | 12/2008 | Higgins | ............... A61B 5/1455 356/39 |
| 2013/0242308 | A1* | 9/2013 | Zhan | .................. G01N 21/8483 356/445 |
| 2016/0025715 | A1* | 1/2016 | DiMagno | .......... B01L 3/502715 506/9 |
| 2020/0005488 | A1* | 1/2020 | Ding | ........................ G06T 7/74 |

* cited by examiner

*Primary Examiner* — Maureen Wallenhorst
(74) *Attorney, Agent, or Firm* — K&L Gates LLP; Louis C. Cullman; Brian J. Novak (57) ABSTRACT

The present disclosure is directed to a method and apparatus for performing an assay on a dry slide or other solid media using a reduced reading window. In an embodiment, method of performing at least one assay comprises obtaining an image of a fluid sample located on a dry slide, positioning a reading window to correspond to an area of the fluid sample in the image, determining an interference area within the reading window based on light intensity, reducing the reading window to eliminate the interference area from the reading window, and performing at least one assay using the reduced reading window.

20 Claims, 7 Drawing Sheets

DRY SLIDE ASSAY USING REDUCED READING WINDOW

PRIORITY CLAIM

The present application claims priority to and the benefit of U.S. Provisional Patent Application No. 62/693,120, filed Jul. 2, 2018, the entirety of which is incorporated herein by reference.

FIELD OF THE DISCLOSURE

The present disclosure relates generally to a method and apparatus that reduces an initial reading window to remove an interference area when performing an assay using an image of a fluid sample on slide media, such as a a dry slide, and more specifically to a method and apparatus that selects a predetermined shape and/or area for a reduced reading window and positions the predetermined shape and/or area within the initial reading window so as to exclude the interference area.

BACKGROUND

In some instances, assays are performed by measuring the light intensity of an area of an image of a fluid sample that has been dispensed on a dry slide or other solid media. A problem that occurs with this method, however, is that when the fluid sample is washed on the dry slide, the washing process can cause imprecision due to stagnation variation from the washing fluid. Some assays, for example, a Digoxin ("DGXN") assay, have poor precision at high analyte levels, particularly in a stagnation area where washing fluid is dispensed, due to unwashed free analyte and free label in the stagnation area.

SUMMARY

The present disclosure is directed to a method and apparatus for performing an assay on a dry slide or other solid media using a reduced reading window. In an example embodiment, which may be used with any other embodiment disclosed herein, a method of performing at least one assay comprises obtaining an image of a fluid sample located on a dry slide, positioning a reading window to correspond to an area of the fluid sample in the image, determining an interference area within the reading window, reducing the reading window to eliminate the interference area from the reading window, and performing at least one assay using the reduced reading window.

In another embodiment, which may be used with any other embodiment disclosed herein, reducing the reading window includes reducing the reading window to a predetermined shape.

In another embodiment, which may be used with any other embodiment disclosed herein, reducing the reading window includes reducing the reading window to a crescent shape.

In another embodiment, which may be used with any other embodiment disclosed herein, reducing the reading window includes reducing the reading window from a circular shape to the crescent shape.

In another embodiment, which may be used with any other embodiment disclosed herein, the reading window has an initial area, and reducing the reading window includes reducing the reading window to a predetermined area less than the initial area.

In another embodiment, which may be used with any other embodiment disclosed herein, the method includes dispensing a washing fluid onto the fluid sample on the dry slide, wherein the interference area is caused by the washing fluid.

In another embodiment, which may be used with any other embodiment disclosed herein, the interference area is caused by fluid stagnation resulting from dispensing the washing fluid.

In another example embodiment, which may be used with any other embodiment disclosed herein, a method of performing at least one assay comprises dispensing a fluid sample on a dry slide, dispensing a washing fluid onto the fluid sample on the dry slide, obtaining an image of the dry slide, positioning a reading window to correspond to an area of the fluid sample in the image, reducing the reading window to exclude an interference area caused by the washing fluid, and performing at least one assay using the reduced reading window.

In another embodiment, which may be used with any other embodiment disclosed herein, the method includes determining the interference area within the reading window based on a known dispense location of the washing fluid.

In another embodiment, which may be used with any other embodiment disclosed herein, reducing the reading window includes reducing the reading window to a predetermined shape.

In another embodiment, which may be used with any other embodiment disclosed herein, reducing the reading window includes reducing the reading window to a crescent shape.

In another embodiment, which may be used with any other embodiment disclosed herein, reducing the reading window includes reducing the reading window from a circular shape to the crescent shape.

In another embodiment, which may be used with any other embodiment disclosed herein, the reading window has an initial area, and reducing the reading window includes reducing the reading window to a predetermined area less than the initial area.

In another embodiment, which may be used with any other embodiment disclosed herein, the interference area is caused by fluid stagnation resulting from dispensing the washing fluid.

In a further example embodiment, which may be used with any other embodiment disclosed herein, an apparatus for performing at least one assay comprises a slide reception location configured to receive at least one dry slide having a fluid sample located thereon, a dispenser configured to dispense a washing fluid onto the fluid sample on the dry slide, and a control unit configured to: (i) position a reading window to correspond to an area of the fluid sample in the image; (ii) reduce the reading window to exclude an interference area caused by the washing fluid; and (iii) perform at least one assay using the reduced reading window.

In another embodiment, which may be used with any other embodiment disclosed herein, the control unit is configured to determine the interference area within the reading window based on a known dispense location of the washing fluid.

In another embodiment, which may be used with any other embodiment disclosed herein, the control unit is configured to reduce the reading window to a predetermined shape.

In another embodiment, which may be used with any other embodiment disclosed herein, the control unit is configured to reduce the reading window from a circular shape to a crescent shape.

In another embodiment, which may be used with any other embodiment disclosed herein, the control unit is configured to reduce the reading window to a predetermined area.

In another embodiment, which may be used with any other embodiment disclosed herein, the interference area is caused by fluid stagnation resulting from the washing fluid being dispensed onto the dry slide.

In another embodiment, which may be used with any other embodiment disclosed herein, any of the structure and functionality disclosed in connection with FIGS. 1 to 11 may be combined with any other structure and functionality disclosed in connection with FIGS. 1 to 11.

In light of the present disclosure and the above aspects, it is therefore an advantage of the present disclosure to provide an improved method and apparatus for determining a reduced reading window for performing an assay of a biological sample.

Additionally, in light of the present disclosure and the above aspects, it is therefore an advantage of the present disclosure to reduce affects from sample washing using a reduced reading window.

The advantages discussed herein may be found in one, or some, and perhaps not all of the embodiments disclosed herein. Additional features and advantages are described herein, and will be apparent from, the following Detailed Description and the figures.

BRIEF DESCRIPTION OF THE DRAWINGS

Embodiments of the present disclosure will now be explained in further detail by way of example only with reference to the accompanying figures, in which.

DETAILED DESCRIPTION

The present disclosure is directed to a method and apparatus for performing an assay on a solid media using a reduced reading window. As discussed in more detail below, the presently disclosed method and apparatus are advantageous, for example, in excluding stagnation areas from imaging to improve imaging precision of biological samples. The stagnation areas may form from one or more processes for washing a sample. By reducing the reading window, light intensity variation in the stagnation areas is selectively excluded from image analysis in performing an assay on a sample.

Figure 1:
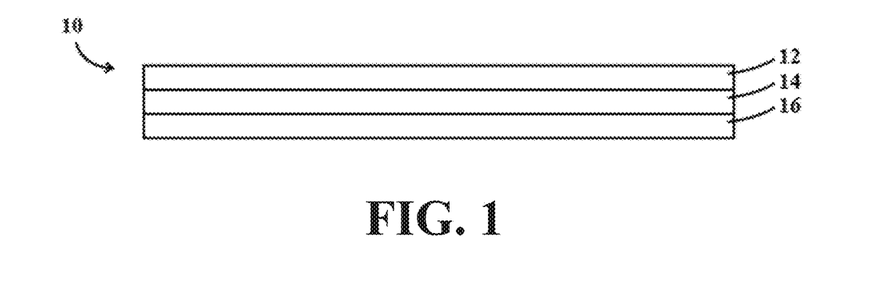
FIG. 1 illustrates a side view of an example embodiment of a dry slide according to the present disclosure.
Figure 2:
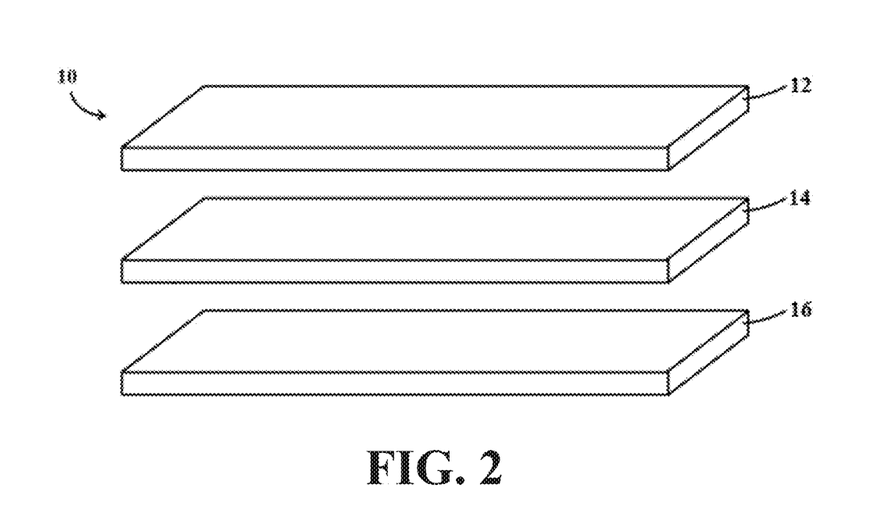
FIG. 2 illustrates an exploded perspective view of the dry slide of FIG. 1.

FIGS. 1 and 2 illustrate an example embodiment of a solid media or dry slide that may be used in accordance with the present disclosure. In FIGS. 1 and 2, the reaction cell is a solid media 10 that may be used with an assay system 20, according to the present disclosure. Solid Media 10 may be, for example, a single or multi-layer thin-film element on which a fluid sample may be dispensed. In the illustrated embodiment, solid media 10 includes a plurality of layers, including a first layer 12 which may be an upper slide mount layer configured to provide a top base layer with an aperture therethrough to receive a fluid sample. The first layer may also be configured to spread the fluid sample thereacross. The solid media 10 also includes a second layer 14, which may be a reagent layer including a reagent configured to react with the fluid sample for a particular assay. The second layer 14 may also include a support layer to provide support or rigidity for the reagent layer. The solid media further includes a third layer 16, which may be a filter layer that provides a low wavelength cutoff filter to be used for an optical analysis. The third layer 16 may include a lower slide mount layer configured to provide a bottom base layer with an aperture therethrough for an optical analysis. While the solid media 10 is shown as a dry slide, in other examples, the solid media may include a reaction cuvette, a dry slide, etc.

Figure 3:
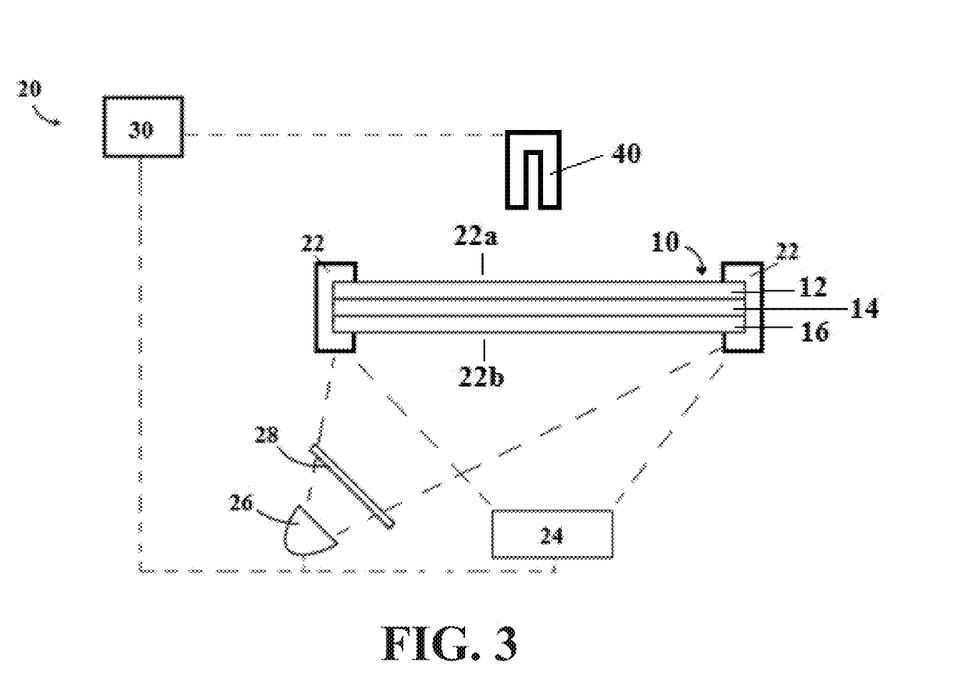
FIG. 3 illustrates a side view of an example embodiment of an assay device holding the dry slide of FIG. 1 according to the present disclosure.

FIG. 3 illustrates an example embodiment of an assay system 20 configured to receive and analyze the solid media 10 to perform an assay. As illustrated, the assay system 20 may include a solid media reception location 22 configured to receive at least one solid media 10 having a fluid sample located thereon, a wash mechanism 40 configured to dispense washing fluid onto solid media 10, an imaging device 24 positioned and arranged relative to the solid media reception location 22 to obtain at least one image of the fluid sample located on the solid media 10, a light source 26 (e.g., one or more light-emitting diode lights) configured to project light onto the solid media 10 so that the light may be modulated by the liquid sample dispensed onto the solid media 10, and optionally an optical filter 28 configured to modulate the light from light source 28 to a particular wavelength specific to the assay being performed.

In the illustrated embodiment, the slide reception location 22 is configured to receive and hold solid media 10 while a fluid sample is added to the first layer 12 of the solid media 10, while washing fluid is added to the first layer 12 of the solid media 10, and/or while the solid media 10 is illuminated by the light source 26 and imaged by the imaging device 24. In the illustrated embodiment, the solid media reception location 22 includes at least one bracket creating a first opening 22a and second opening 22b. The fluid sample and washing fluid may be added to the solid media 10 (e.g., through an aperture in the first layer 11) at the first opening 22a of the solid media reception location 22, while the second opening 22b of the solid media reception location 22 allows the solid media 10 to be illuminated and imaged (e.g., through an aperture in the sixth layer 16) once the fluid sample has reacted with the reagent. It should further be understood that the addition of the fluid sample and washing fluid may occur before the solid media 10 is received by the solid media reception location 22, and that the illumination and imaging of the solid media 10 can occur at the first opening 22a at the top of solid media reception location 22 as opposed to the second opening 22b at the bottom of the solid media reception location 22.

The assay system 20 may further include a control unit 30 configured to control one or more of the elements of assay system 20 and analyze the fluid sample on the solid media 10 in accordance with the method described herein. Control unit 30 may include a processor and a non-transitory memory storing instructions for performing the method, wherein the processor executes the instructions to control one or more elements of assay system 20 and perform the assay.

Figure 4:
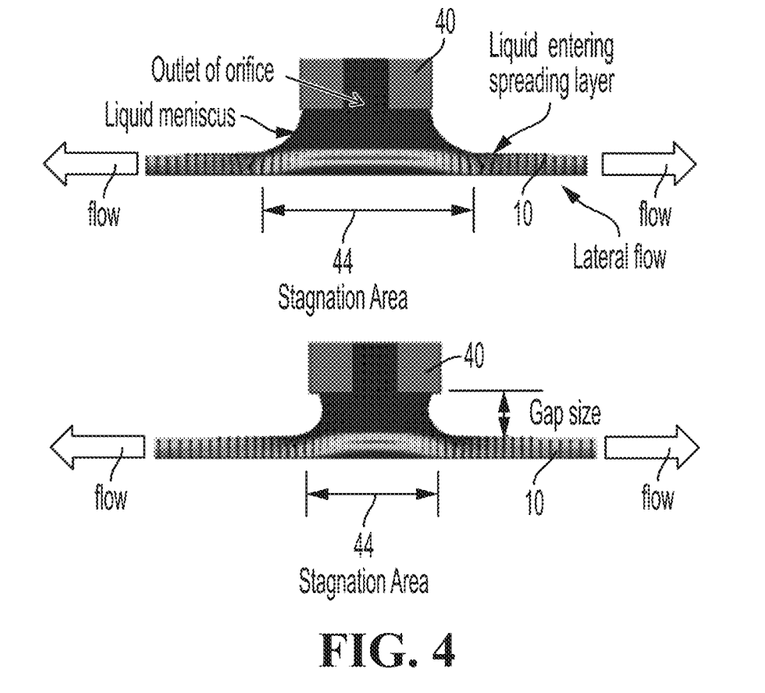
FIG. 4 illustrates an example embodiment of a wash mechanism that dispenses washing fluid onto a dry slide in accordance with the present disclosure.
Figure 6:
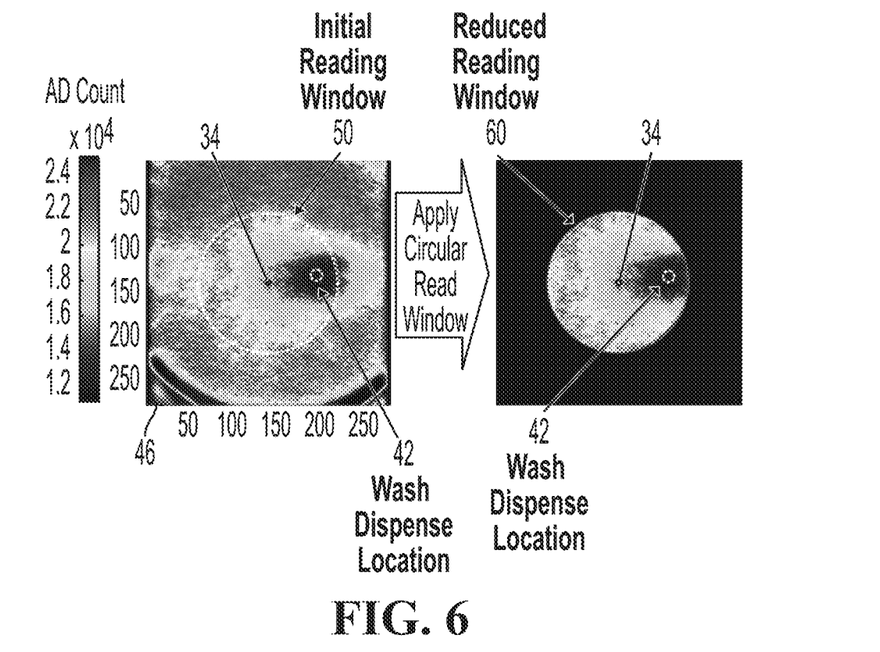
FIG. 6 illustrates an example embodiment of a reading window being created within an image in accordance with the present disclosure.
Figure 7:
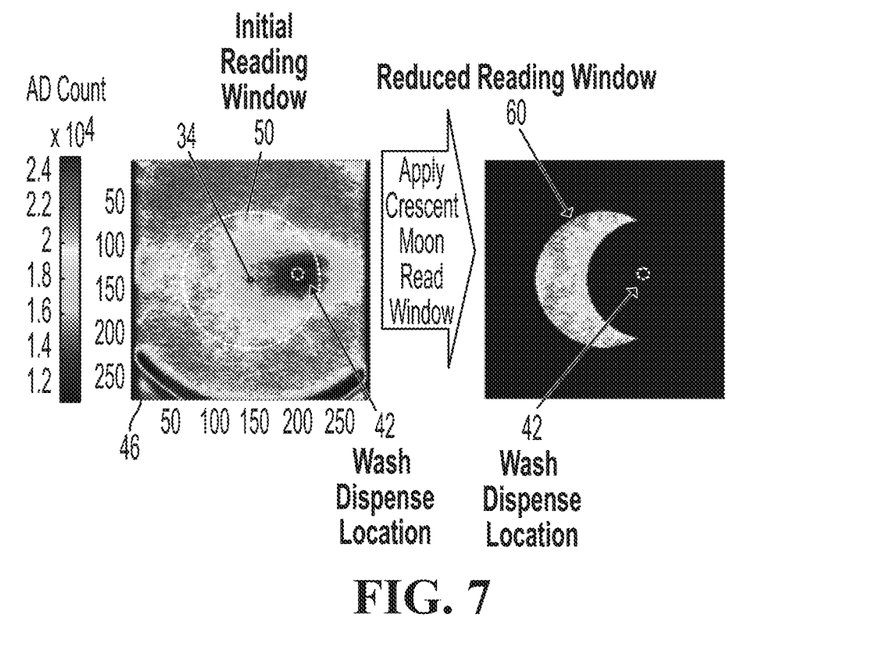
FIG. 7 illustrates an example embodiment of an initial reading window being reduced to a reduced reading window in accordance with the present disclosure.

FIG. 4 illustrates an example embodiment of washing fluid being dispensed onto the solid media 10, according to an example embodiment of the present disclosure. In the illustrated embodiment, the washing fluid may be dispensed onto the solid media 10 via the wash mechanism 40 controlled by the control unit 30, though the washing fluid may also be dispensed prior to the solid media 10 being accepted at the solid media reception location 22. As illustrated, the wash mechanism 40 is positioned over a solid media 10, which includes a fluid sample, and the washing fluid is dispensed onto the solid media 10 at a wash dispense location 42 (as shown in FIGS. 6 and 7). In an embodiment, the washing fluid is applied by a nozzle (e.g., a tip with a small orifice about 0.4 millimeters ("mm") in diameter) of the wash mechanism 40 at about 2 mm away from the center of a sample dispense location 34 (shown in FIGS. 6 and 7) where the fluid sample was dispensed on the solid media 10. The washing fluid may be dispensed at a dispensing rate and total dispensing volume specific for the type of assay being performed.

As illustrated in the example of FIG. 4, when the washing fluid is dispensed, a small liquid meniscus is formed between the nozzle and the solid media 10. The washing fluid enters the solid media 10 near the edge of the meniscus. Under the meniscus, a stagnation area 44 is formed with little fluid flow, causing free label and analyte to remain within the stagnation area 44 without significant displacement. Outside the meniscus, lateral fluid flow displaces soluble materials (including free label and free analytes) out from the center under the nozzle of the wash mechanism 40.

The size of the stagnation area 44 is affected by the fluid flow rate from nozzle, the flow rate through the solid media 10, and the gap size between the nozzle and the solid media 10. While the flow rate from the nozzle may be controlled by the control unit 30, the flow rate in the solid media 10 is significantly affected by sample fluid viscosity, which varies from patient to patient. The flow rate in the solid media 10 may also be affected by specific properties of the solid media 10 (e.g., wettability, permeability and porosity) that depend on the specific composition of the solid media 10. As a result, the size of the stagnation area 44 has large variability from sample to sample, meaning that the amount of unwashed free label and free analyte also varies from sample to sample. The variation of the free label and free analyte in the stagnation area 44 contributes to variation in image reflectance density and therefore the rate of bound label determination.

To correct for the free label and free analyte in the stagnation area 44, the control unit 30 may employ algorithms to actively identify and utilize areas on the solid media 10 with minimum interference from unwanted signals, such as from free label and free analyte from the washing fluid. The algorithms cause a reduction of an initial reading window 50 (shown in FIG. 7) to avoid an interference area from washing variations, thereby eliminating the variation in the washing stagnation area from the assay signal and improving assay precision. In a specific embodiment explained in more detail below an initial circular reading window 50 can be reduced to a reduced crescent-shaped reading window 60.

Figure 5:
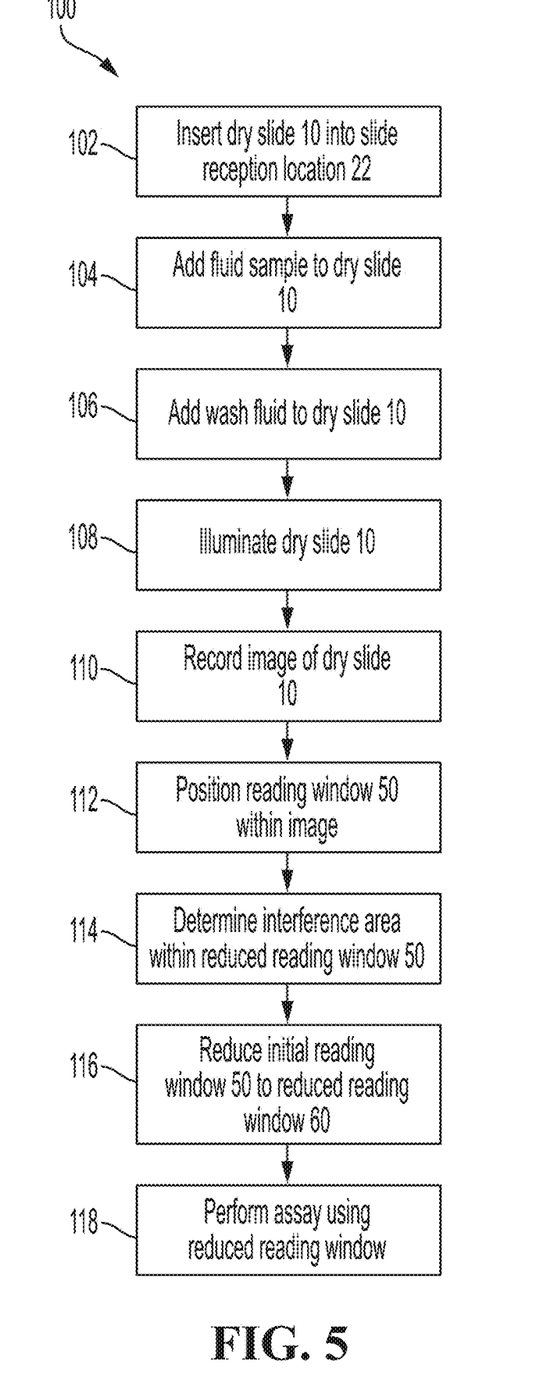
FIG. 5 illustrates an example embodiment of a method of performing at least one assay in accordance with the present disclosure.

FIG. 5 illustrates a method 100 of performing at least one assay using, for example, the solid media 10 and the assay system 20. Those of ordinary skill in the art will understand that method 100 may also be used with different types of solid media and assay systems. It should also be understood that one or more of the steps shown in FIG. 5 can be omitted and/or additional steps can be added, and/or the order of certain steps can be rearranged, without departing from the spirit and scope of the present disclosure.

Beginning at step 102, a solid media 10 is received at the solid media reception location 22. In an embodiment, the solid media 10 includes an antibody, which is either coated throughout a beaded spreading layer (non-receptor format, e.g., the Digoxin assay format) or in a thin receptor layer (receptor format, e.g., carbamazepine). For example, an HRP (Horseradish peroxidase) label may be gravure coated with prebinding (in non-receptor format) or without prebinding (receptor format). Those of ordinary skill in the art will understand that different types of solid media 10 may be used for different types of assays, and that the composition and coating of the solid media 10 may therefore change. In the illustrated embodiment, the assay system 20 is configured to receive a plurality of different types of solid media, and to perform different types of assays and/or multiple assays depending on which type of solid media is inserted into the solid media reception location 22.

At step 104, a fluid sample to be analyzed is dispensed onto the solid media 10 at a sample dispense location 34. For example, a small amount (e.g., about 11 μL) of sample fluid with free analyte may be metered onto the solid media 10 at the sample dispense location 34. In an embodiment, the sample fluid is added at the sample dispense location 34 of the solid media 10, for example, by a pipette controlled by the control unit 30. In another embodiment, the fluid sample may be added by a user prior to insertion of the solid media 10 into the solid media reception location 22. The fluid sample may then spread though the first layer 12 and mix with the reagent included with the second layer 14. In the HRP embodiment discussed above, the gravure coated HRP label may be hydrated and dissolved by the sample fluid, and the analyte in the sample fluid and the dissolved HRP label may bind with the antibody competitively for the limited antibody sites for a certain amount of time (e.g., typically 5 minutes).

At step 106, washing fluid is dispensed onto the fluid sample on solid media 10, for example, at a wash dispense location 42 that is close to, but different from, the sample dispense location 34 (e.g., about 2 mm off of the center of the location where the fluid sample was dispensed on the solid media). The washing fluid may be applied, for example, by the wash mechanism 40 as illustrated in FIG. 4 above. Alternatively, the washing fluid may be added by a user prior to insertion of the solid media 10 into the solid media reception location 22. In the HRP embodiment discussed above, the unbound label and unbound analyte may be washed away by washing fluid which contains $H_2O_2$ for initializing the dye generation reactions, wherein the concentration of the bound label is monitored by the dye generation rate.

At step 108, the light source 26 may project light onto the solid media 10 so that the light may be modulated by the fluid sample dispensed onto the solid media 10. In an embodiment, the light is modulated by the optical filter 28 and/or a filter provided by the solid media 10 (e.g., at the third layer 16) so as to project a specific wavelength for the assay being performed. In an embodiment, the wavelength needed may be programmed into the control unit 30, which may then control the light source 26 and the optical filter 28 so that the correct wavelength light for the assay being performed is projected onto the solid media 10.

At step 110, the imaging device 24 records at least one image of the fluid sample dispensed onto the solid media 10. The image may be recorded, for example, while the light source 26 projects light onto the solid media 10 to be modulated by the liquid sample dispensed onto the solid media 10 and/or while the optical filter 28 modulates the light from the light source 28. The imaging device 24 may be, for example, a charge-coupled device ("CCD") camera, which may, for example, record a two-dimensional image showing an approximately elliptical or circular fluid sample on the solid media 10. In an embodiment, the image is taken at a specified wavelength and then the light intensity (e.g., AD Count) is converted in the center area (i.e., at sample dispense location 34) with 4.5 mm diameter into reflectance density.

At step 112, the control unit 30 positions a reading window 50 to correspond to an area of the fluid sample in the image. The reading window 50 may be positioned, for example, by selecting a target location and then forming the reading window 50 with a predetermined area and/or shape around the target location. The target location may be, for example, the sample dispense location 34 or another default location (e.g., the default center of the solid media 10), or may be chosen based on light intensity. U.S. Provisional Application No. 62/693,110, entitled "Method and Apparatus for Selecting Dry Slide Image Read Location", filed on the same day as the present application, further describes a method for locating a target location on a solid media, and is incorporated herein by reference and relied upon. In an embodiment, the initial reading window 50 can be placed using a known sample dispense location 34 as a central point. In an alternative embodiment, the reading window 50 may be positioned or sized based on a detected light intensity from the image, for example, wherein the reading window 50 is drawn to include or exclude a range of light intensities/reflectance densities.

FIG. 6 illustrates an example embodiment of an initial reading window 50 being positioned within an image 46 taken by the imaging device 30. In FIG. 6, the left image shows the light intensity (e.g., AD count) of a larger area of the solid media 10, while the right image shows the light intensity once the area outside of the initial reading window 50 has been excluded. In the illustrated embodiment, the initial reading window 50 has been positioned by taking the sample dispense location 34 and creating a circle at a specified diameter around the sample dispense location 34 such that all light intensity (or substantially at least 90% of the original light intensity) outside of the circle is thereafter excluded. Those of ordinary skill in the art will recognize that other shapes can be used for the reading window 50, though the circular flow of the sample from the sample dispense location 34 when the sample is added to the solid media 10 makes a circle particularly indicative of the overall sample.

Returning to FIG. 5, at step 114, an interference area within the initial reading window 50 may be determined. The interference area may be focused, for example, at the central point of the wash dispense location 42, where the stagnation area 44 forms due to variation in the free label and analytes, which contributes to variation in dye generation, and therefore the variation in the light intensity signal. As illustrated in FIG. 6, the light intensity in the stagnation area 44 dramatically differs from that of the rest of the reading window 50, with lateral fluid flow where most of free label and free analytes are removed. Since the washing fluid was dispensed off-center from the location where the sample was dispensed, the stagnation area 44 likewise is located off-center from the center of the reading window 50, which is focused at the center of the fluid sample. The stagnation area 44 is darker due to dye generation from both bound and free labels. The variation caused by the stagnation area 44 has a relatively large contribution to image signal, thereby making assay analysis less precise and prone to errors. In an alternative embodiment, the interference area may be determined based on light intensity profiles without knowing wash dispense location 42, wherein the peak or valley of the light intensity profile is the center of the interference.

At step 116 of FIG. 5, the initial reading window 50 is reduced to a smaller area (as shown in FIG. 6) to eliminate the interference area and create a reduced reading window 60. The reduced reading window 60 may be used to perform the assay, thereby minimizing the effects of the wash stagnation variation. In the illustrated embodiment, the reading window 50 is reduced to a crescent-shaped reading window 60. The center of the outside or larger diameter of the crescent-shape is placed to match up to the target location used as the center to create the initial reading window 50. In an embodiment, the control unit 30 is configured to place the crescent-shaped reading window 60 by selecting the center of the crescent-shaped reading window 60 to correspond to the center of the circular reading window 50, and by rotating the crescent shape so that the detected interference area lies in the excluded portion of the crescent shape. In another embodiment, the control unit 30 is configured to place the crescent-shaped reading window 60 by selecting the center of the excluded area to correspond to the wash dispense location 42, and by excluding a circular area smaller than the reading window around the wash dispense location 42.

FIG. 7 illustrates an example embodiment in which the reading window 50 from FIG. 6 is reduced to remove the stagnation area 44. In FIG. 7, the left image shows the light intensity of a larger area of the solid media 10, while the right image shows the light intensity once the reduced reading window 60 has been placed to exclude the stagnation area 44. In the illustrated embodiment, an area with a diameter of 3 mm and centered at 1.4 mm off the sample dispense location 34 is removed from the original 4.5 mm initial circular reading window 50 at the sample dispense location 42. That is, the initial reading window 50 may be formed as a circle around the sample dispense location 34 (e.g., a 4.5 mm perimeter around the sample dispense location 34), while the reduced reading window may then be formed to exclude a smaller circle around the wash dispense location 42 (e.g., a 3 mm perimeter around wash dispense location 42).

In the illustrated embodiment, both the initial circular reading window 50 and the reduced crescent-shaped reading window 60 are predetermined shapes. Although FIG. 7 shows a circular reading window being reduced to a crescent shape, it should be understood that different types of reductions are contemplated. For example, an elliptical reading window may be reduced to a crescent shape or other smaller area, a square, rectangular or other uniform or symmetric window may be reduced to a smaller square, rectangle or other uniform or non-uniform area with a portion excluded, or an abstract or non-uniform shape may be reduced to include an excluded portion to remove the dark interference area caused by fluid stagnation. It is advantageous to remove a circle from the initial reading window to create the reduced reading window because wash flow is almost axis-symmetric corresponding to the wash dispense location.

In another embodiment, one or both of the shapes of the initial reading window 50 and the reduced reading window 60 may not be predetermined. For example, the area and/or shape of the reduced reading window 60 may be determined at the time that step 116 is performed, for example, by excluding a portion of the initial reading window 50 based on a detected light intensity from the image being above or below a threshold or within a particular range.

At step 118 of FIG. 5, an assay is performed using the reduced reading window 60. The assay may be performed, for example, by taking an average optical intensity across the reduced reading window 60. In an embodiment, the reduced reading window 60 is used to determine the light intensity as function of time. For example, the rate of the light intensity (signal) change may be used to calculate the response (the rate of change) for predicting assay concentration.

It has been determined that reducing the reading window as disclosed herein effectively reduces variations from free label and free analytes and therefore improves assay precision.

Figure 8:
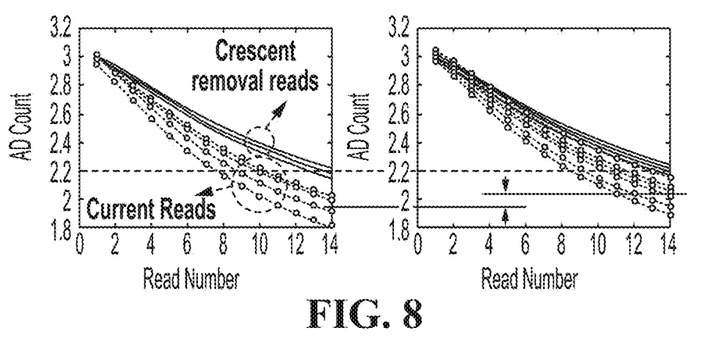
FIG. 8 illustrates an example of how the method according to the present disclosure improves Digoxin kinetics.

FIG. 8 shows kinetics (signal change as function of time) for the assay DGXN with calibrator level 3. As illustrated, there are smaller variations with a reduced, crescent-shaped reading window as compared to a circular reading window. The lower current reads curves correspond to the circular reading window with center at predefined sample dispense location. The upper crescent removal reads curves correspond to the crescent-shaped reading window. As illustrated, the upper curves are more repeatable (more tightly distributed), while the lower curves are less repeatable. In FIG. 8, the left and right plots compare the results between the same samples but from different cups. As illustrated, the crescent-shaped reading window generates better accuracy between the two cups compared to the circular reading window.

Figure 9:
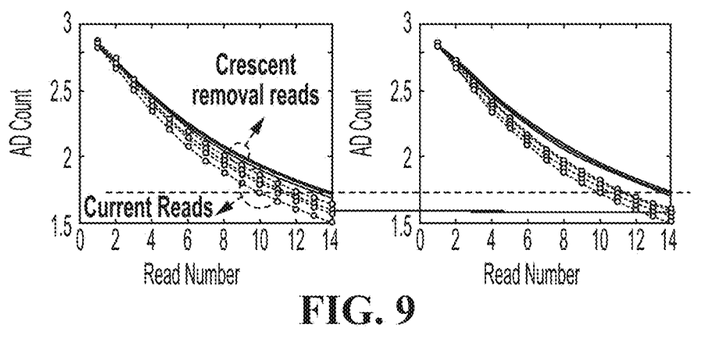
FIG. 9 illustrates an example of how the method according to the present disclosure improves Digoxin kinetics.

FIG. 9 shows kinetics (signal change as function of time) for the assay DGXN with calibrator level 3. As illustrated, there are smaller variations with a reduced, crescent-shaped reading window as compared to a circular reading window. The lower current reads curves correspond to the circular reading window with center at predefined sample dispense location. The upper crescent removal reads curves correspond to the crescent-shaped reading window. As illustrated, the upper curves are more repeatable (more tightly distributed), while the lower curves are less repeatable. In FIG. 9, the left and right plots compare the results between the same samples but from different cups. As illustrated, the crescent-shaped reading window generates better accuracy between the two cups compared to the circular reading window.

Figure 10:
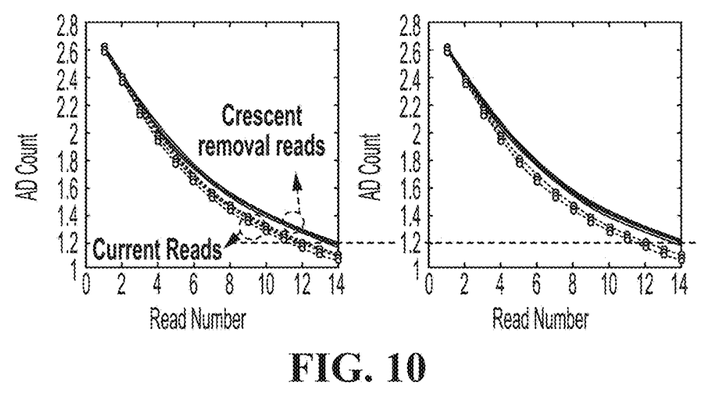
FIG. 10 illustrates an example of how the method according to the present disclosure improves Digoxin kinetics.

FIG. 10 shows kinetics (signal change as function of time) for the assay DGXN with calibrator level 3. As illustrated, there are smaller variations with a reduced, crescent-shaped reading window as compared to a circular reading window. The lower current reads curves correspond to the circular reading window with center at predefined sample dispense location. The upper crescent removal reads curves correspond to the crescent-shaped reading window. As illustrated, the upper curves are more repeatable (more tightly distributed), while the lower curves are less repeatable. In FIG. 10, the left and right plots compare the results between the same samples but from different cups. As illustrated, the crescent-shaped reading window generates better accuracy between the two cups compared to the circular reading window.

Figure 11:
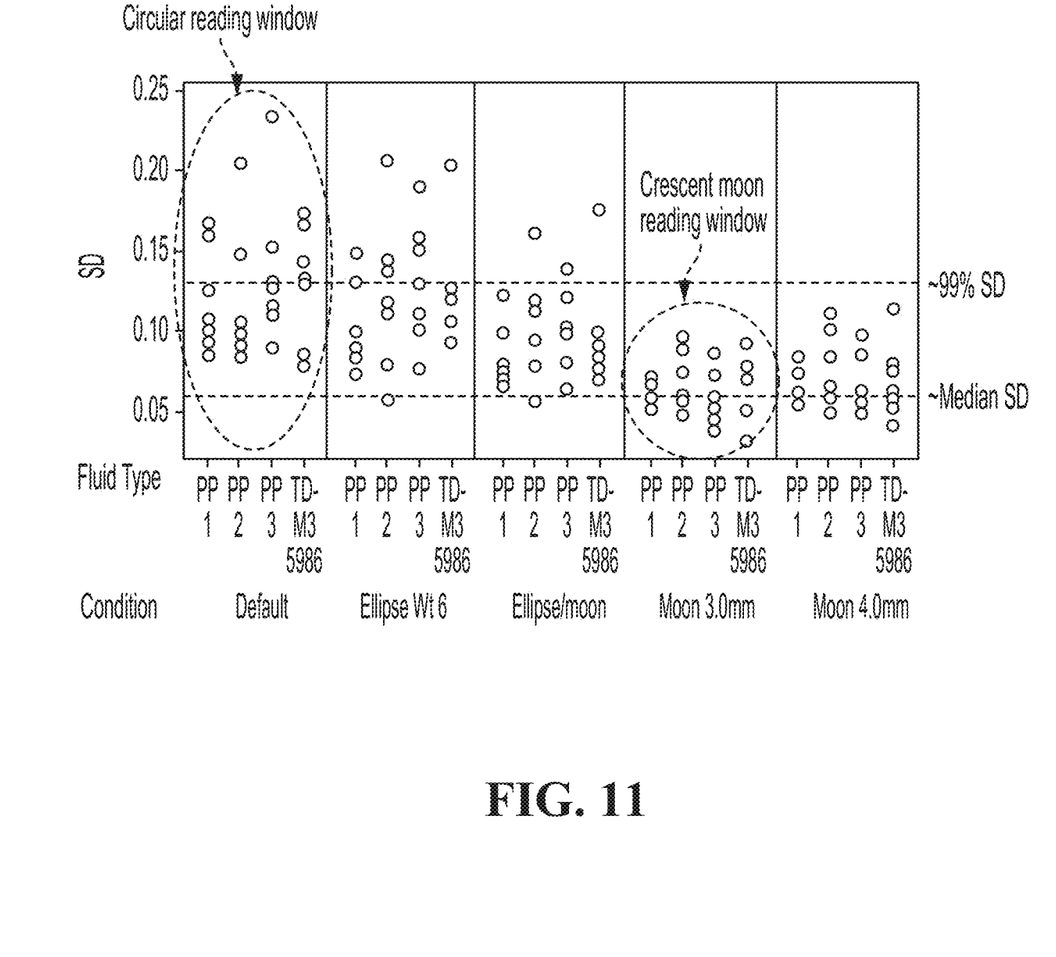
FIG. 11 illustrates an example of how the method according to the present disclosure improves assay precision using reduced reading windows.

FIG. 11 is a chart showing performance with different reading window shapes. To create the graphs shown in FIG. 11, seven different instruments and four different fluid types with high Digoxin concentration (patient 1, 2, 3, and TDM3 fluid) were used in tests. In FIG. 11, the default is a 4.5 mm circular reading window. The Ellipse Wt6 is a 4.5 mm×3.4 mm ellipse reading window. The Ellipse/Moon is a 4.5 mm×3.4 mm ellipse reading window with removal of the washing stagnation area. The Moon 3.0 mm is a 4.5 mm circular reading area with a 3 mm and 1.4 mm offset washing stagnation area removal (the crescent moon reading window). The Moon 4.0 mm is a 4.5 mm circular reading area with a 4 mm and 2.5 mm offset washing stagnation area removal. The best performance was from the 4.5 mm circular reading window with the 3 mm stagnation area removal at offset of 1.4 mm (the crescent moon reading window). FIG. 11 therefore shows the best precision with a crescent moon shaped reading window across all analyzers and all fluids with offset of 1.4 mm and 3 mm circular removal.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the disclosure and does not pose a limitation on the scope of the disclosure otherwise claimed. No language in the specification should be construed as indicating any non-claimed element essential to the practice of the disclosure.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of the disclosure are described herein, including the best mode known to the inventors for carrying out the disclosure. Of course, variations on those preferred embodiments will become apparent to those of ordinary skill in the art upon reading the foregoing description. The inventor expects those of ordinary skill in the art to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the disclosure so claimed are inherently or expressly described and enabled herein.

Further, it is to be understood that the embodiments of the disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

The invention is claimed as follows:

1. A method of performing at least one assay comprising:
   obtaining, in a processor of a control unit, an image of a fluid sample located on a dry slide;
   positioning, via the processor of the control unit, a reading window to correspond to an area of the fluid sample in the image;
   determining, via the processor of the control unit, an interference area within the reading window based on light intensity;
   reducing, via the processor of the control unit, the reading window to eliminate the interference area from the reading window; and
   performing, via the control unit, at least one assay using the reduced reading window.

2. The method of claim 1, wherein reducing the reading window includes reducing the reading window to a predetermined shape.

3. The method of claim 2, wherein reducing the reading window includes reducing the reading window to a crescent shape.

4. The method of claim 3, wherein reducing the reading window includes reducing the reading window from a circular shape to the crescent shape.

5. The method of claim 1, wherein the reading window has an initial area, and wherein reducing the reading window includes reducing the reading window to a predetermined area less than the initial area.

6. The method of claim 1, which includes dispensing a washing fluid onto the fluid sample on the dry slide, wherein the interference area is caused by the washing fluid.

7. The method of claim 6, wherein the interference area is caused by fluid stagnation resulting from dispensing the washing fluid.

8. A method of performing at least one assay comprising:
   dispensing a fluid sample on a dry slide;
   dispensing a washing fluid onto the fluid sample on the dry slide;
   obtaining, via a processor of a control unit, an image of the dry slide;
   positioning, via the processor of the control unit, a reading window to correspond to an area of the fluid sample in the image;
   reducing, via the processor of the control unit, the reading window to exclude an interference area caused by the washing fluid; and
   performing, via the control unit, at least one assay using the reduced reading window.

9. The method of claim 8, which includes determining the interference area within the reading window based on a known dispense location of the washing fluid.

10. The method of claim 8, wherein reducing the reading window includes reducing the reading window to a predetermined shape.

11. The method of claim 10, wherein reducing the reading window includes reducing the reading window to a crescent shape.

12. The method of claim 11, wherein reducing the reading window includes reducing the reading window from a circular shape to the crescent shape.

13. The method of claim 8, wherein the reading window has an initial area, and wherein reducing the reading window includes reducing the reading window to a predetermined area less than the initial area.

14. The method of claim 8, wherein the interference area is caused by fluid stagnation resulting from dispensing the washing fluid.

15. An apparatus for performing at least one assay comprising:
   a slide reception location configured to receive at least one dry slide having a fluid sample located thereon;
   a dispenser configured to dispense a washing fluid onto the fluid sample on the at least one dry slide; and
   a control unit configured to: (i) obtain an image of the fluid sample on the at least one dry slide; (ii) position a reading window to correspond to an area of the fluid sample in the image; (iii) reduce the reading window to exclude an interference area caused by the washing fluid; and (iv) perform at least one assay using the reduced reading window.

16. The apparatus of claim 15, wherein the control unit is configured to determine the interference area within the reading window based on a known dispense location of the washing fluid.

17. The apparatus of claim 15, wherein the control unit is configured to reduce the reading window to a predetermined shape.

18. The apparatus of claim 15, wherein the control unit is configured to reduce the reading window from a circular shape to a crescent shape.

19. The apparatus of claim 15, wherein the control unit is configured to reduce the reading window to a predetermined area.

20. The apparatus of claim 15, wherein the interference area is caused by fluid stagnation resulting from the washing fluid being dispensed onto the at least one dry slide.

\* \* \* \* \*